US00PP20203P2

(12) United States Plant Patent
Klemm

(10) Patent No.: US PP20,203 P2
(45) Date of Patent: Aug. 4, 2009

(54) *SANVITALIA* PLANT NAMED 'KLESP07168'

(50) Latin Name: *Sanvitalia procumbens*
Varietal Denomination: KLESP07168

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/082,132

(22) Filed: Apr. 9, 2008

(51) Int. Cl.
*A01H 5/00* (2006.01)

(52) U.S. Cl. ..... Plt./476

(58) Field of Classification Search ..... Plt./263, Plt./476

See application file for complete search history.

*Primary Examiner*—Susan B McCormick Ewoldt
(74) *Attorney, Agent, or Firm*—Jondle & Associates, P.C.

(57) ABSTRACT

A new cultivar of *Sanvitalia* particularly characterized by long-lasting, yellow, single flowers with multiple whorls of ray florets, a mounding and trailing plant habit, a vigorous growth habit with good branching and strong tolerance to heat, is disclosed.

1 Drawing Sheet

Genus and species: *Sanvitalia procumbens*.
Variety denomination: 'KLESP07168'.

BACKGROUND OF THE NEW PLANT

The present invention comprises a new and distinct cultivar of *Sanvitalia,* botanically known as *Sanvitalia procumbens* and hereinafter referred to by the cultivar name 'KLESP07168'. 'KLESP07168' was discovered as a seedling resulting from an open pollination among unnamed *Sanvitalia* (upatented) plants conducted in May 2005 in Stuttgart, Germany. A single plant selection was subsequently chosen for further evaluation and for asexual propagation.

The new cultivar was created in 2005 in Stuttgart, Germany and has been asexually reproduced repeatedly by vegetative cuttings and in-vitro propagation in Stuttgart, Germany over a two-year period (about 7 generations). 'KLESP07168' has been found to retain its distinctive characteristics through successive asexual propagations.

Plant Breeder's Rights for this cultivar were applied for in Canada on Mar. 1, 2007 and in Switzerland on Jul. 6, 2007. 'KLESP07168' has not been made publicly available more than one year prior to the filing date of this application.

SUMMARY OF THE INVENTION

The following are the most outstanding and distinguishing characteristics of this new cultivar when grown under normal commercial practices in a greenhouse in Suttgart, Germany.

1. Long-lasting, yellow, single flowers with multiple whorls of ray florets;
2. A mounding and trailing plant habit;
3. A vigorous growth habit with good branching; and
4. Strong tolerance to heat.

DESCRIPTION OF THE PHOTOGRAPH

This new *Sanvitalia* plant is illustrated by the accompanying photograph which shows a close-up of the mature flowers, buds and foliage; the colors shown are as true as can be reasonably obtained by conventional photographic procedures. The photograph is of a plant about 3-months old and grown from rooted cuttings in 10-cm pots in a greenhouse (glasshouse) in Stuttgart, Germany between February and April under conditions which approximate those generally used in commercial practice.

DESCRIPTION OF THE NEW CULTIVAR

The following detailed descriptions set forth the distinctive characteristics of 'KLESP07168'. The data which define these characteristics were collected from asexual reproductions carried out in Stuttgart, Germany. The plant history was taken on 2-month old plants in 10-cm pots that were pinched once and grown in a greenhouse in the spring. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Asteraceae.
- *Genus and species.*—*Sanvitalia procumbens.*
- *Common name.*—*Sanvitalia.*

Plant:
- *Form and habit.*—Mounding and trailing.
- *Growth and branching habit.*—Medium-vigor with good branching.
- *Height (from top of soil).*—6 cm.
- *Width (including flowers).*—10 cm.
- *Time to produce a finished flowering plant.*—45 days.
- *Outdoor plant performance.*—Very good.
- *Time to initiate and develop roots.*—20 days.
- *Root description.*—Fine, white, moderate branching.

Stems:
- *Length.*—10 cm.
- *Diameter.*—0.2 cm.
- *Internode length.*—1 cm to 3 cm.

*Color.*—RHS 144C and RHS 144D (Reddish-green) but sometimes Reddish-brown.

*Texture.*—Smooth.

*Anthocyanin.*—Absent.

Leaves:

*Arrangement.*—Simple and opposite.

*Shape.*—Elliptical.

*Apex.*—Obtuse.

*Base.*—Obtuse.

*Margin.*—Entire.

*Size, immature leaves.*—Length. 0.8 cm. Width: 0.6 cm.

*Size, mature leaves* (*fully expanded*).—Length: 2.5 cm. Width: 1 cm.

*Color, immature leaves.*—Upper surface: RHS 137A (medium-green). Lower surface: RHS 138B (light-green).

*Color, mature leaves.*—Upper surface: RHS 137A (medium-green). Lower surface: RHS 138B (light-green).

*Venation.*—Type: Palmate. Color: RHS 138D (light-green).

*Texture.*—Smooth.

Flower bud:

*Shape.*—Round.

*Diameter.*—0.3 cm.

*Length.*—0.4 cm.

*Color* (*at tight bud, when starting to show color*).—Light-green.

Inflorescence:

*Type.*—Composite-type, solitary inflorescences born terminally above the foliage.

*Quantity of inflorescences per plant.*—15 to 25.

*Lastingness of individual blooms on the plant.*—More than 2 weeks.

*Fragrance.*—Absent.

*Inflorescence diameter.*—Immature: 1 cm. Mature: 2 cm.

*Disc diameter.*—0.4 cm.

*Disc floret.*—Quantity (per inflorescence): 30. Shape: Round. Tube color: Immature: RHS 139D (green). Mature: RHS 139D (green). Length: 0.4 cm. Diameter (at apex): 0.05 cm. Apex: Acute. Apex color: Light green to nearly white. Base: Fused.

*Ray floret.*—Quantity: 25. Shape: Obovate. Color, immature: Upper surface: RHS 12B (Yellow) and becomes more intense towards the base, RHS 13A and RHS 14A. Lower surface: RHS 12A (Yellow) with green veins. Color, mature: Upper surface: RHS 12B (Yellow) and becomes more intense towards the base, RHS 13A and RHS 14A. Lower surface: RHS 12A (Yellow) with green veins. Length: 0.8 cm. Width: 0.4 cm. Apex: Obtuse. Base: Acute. Margin: Serrate at the apex. Texture: Smooth.

*Penduncle.*—Color: RHS 144C and RHS 144D (Reddish-green). Length: 2 cm. Diameter: 0.1 cm. Texture: Smooth.

*Phyllaries.*—Quantity (per inflorescence): 5. Shape: Lanceolate. Color: Upper surface: RHS 137A (Green). Lower surface: RHS 138B (Light-green). Length: 0.5 cm. Width: 0.2 cm. Apex: Obtuse. Base: Obtuse. Margin: Entire. Texture: Smooth.

Reproductive organs:

*Androecium.*—Location: On disc florets. Stamens: Too small to determine characteristics. Pollen color: Yellow. Pollen amount: Sparse.

*Gynoecium.*—Location: On ray florets. Pistil length: 0.4 cm. Pistil quantity: 1 per ray flower. Stigma: Color: RHS 187A (Dark violet-brown). Shape: In 2 parts at the top. Style: Length: 0.4 cm. Color: RHS 187A (Dark violet-brown).

Fruit and seed set: Seeds are small, round, 0.05 cm wide and dark brown/black in color.

Disease and insect resistance: Not observed.

COMPARISON WITH PARENTAL AND COMMERCIAL CULTIVARS

'KLESP07168' differs from the parent, a typical unnamed individual *Sanvitalia* plant in that 'KLESP07168' multiple rows of ray florets when compared to a typical individual *Sanvitalia* plant.

'KLESP07168' differs from the commercial comparison variety, 'Yellow Sprite' (patent status unknown) in that 'KLESP07168' has more whorls of ray florets and a more compact plant habit than 'Yellow Sprite'.

I claim:

1. A new and distinct cultivar of *Sanvitalia* plant as shown and described herein.

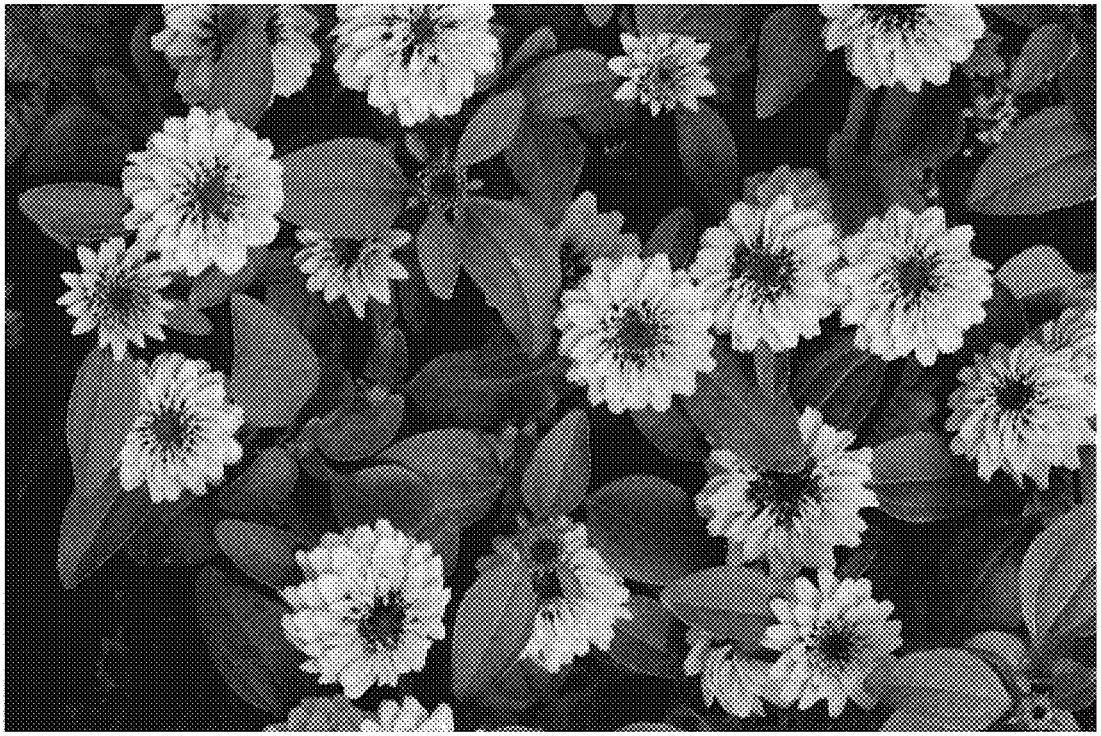

* * * * *